United States Patent [19]

Leurink

[11] Patent Number: 4,496,362

[45] Date of Patent: Jan. 29, 1985

[54] CONTAINER FOR LIQUIDS FOR USE IN MEDICINE AND SURGERY

[75] Inventor: Hendrik J. Leurink, Torenwer, Netherlands

[73] Assignee: Stichtig Centraal Laboratorium Van De Bloedtrasfusiedienst Van Het Nederlandse Rode Kruis, Amsterdam, Netherlands

[21] Appl. No.: 570,519

[22] Filed: Jan. 12, 1984

Related U.S. Application Data

[63] Continuation of Ser. No. 197,476, Oct. 16, 1980, Pat. No. 4,439,192, which is a continuation of Ser. No. 95,975, Nov. 20, 1979, abandoned, which is a continuation of Ser. No. 869,102, Jan. 13, 1978, abandoned, which is a continuation of Ser. No. 690,731, May 27, 1976, abandoned.

[30] Foreign Application Priority Data

May 30, 1975 [GB] United Kingdom ............... 23632/75

[51] Int. Cl.³ ............................................... A61M 5/00

[52] U.S. Cl. .................................... 604/408; 604/415; 206/610

[58] Field of Search ............... 206/438, 610, 632, 615; 150/8; 604/403, 408, 410, 415, 905

[56] References Cited

U.S. PATENT DOCUMENTS

| | | | |
|---|---|---|---|
| 2,838,046 | 6/1958 | Butler | 128/214 D |
| 3,209,752 | 10/1965 | Bujan et al. | 128/272 |
| 3,211,144 | 10/1965 | Nehring | 128/272 |
| 3,327,709 | 6/1967 | Nehring et al. | 128/272 |
| 3,336,924 | 8/1967 | Sarnoff et al. | 128/272.3 |
| 3,342,326 | 9/1967 | Zackheim | 128/272 |
| 3,509,879 | 5/1970 | Bathish et al. | 128/214 D |
| 3,788,374 | 1/1974 | Saijo | 128/214 B |

FOREIGN PATENT DOCUMENTS

| | | | |
|---|---|---|---|
| 1411863 | 10/1975 | United Kingdom | 128/214 D |

*Primary Examiner*—Michael H. Thaler
*Attorney, Agent, or Firm*—Larson and Taylor

[57] ABSTRACT

A container for liquids for use in medicine and surgery is made of flexible plastics material and a container volume is defined by heat seals at each end of the container. At one end of the container there are three ports one being a filling tube and the other two being outlet or additive ports which are sealed by frangible membranes. To allow for expansion of air in the volumes outside those membranes the outer end of each of those ports open into expansion chambers defined by further heat sealed seams of the sheet or tube material forming the container. A line of weakening enables these expansion chambers to be torn off immediately before the use of the appropriate port so as to gain access to the port but so as meanwhile to have preserved the sterility of the outer surface of the membrane.

8 Claims, 6 Drawing Figures

CONTAINER FOR LIQUIDS FOR USE IN MEDICINE AND SURGERY

This application is a continuation of application Ser. No. 197,476, filed Oct. 16, 1980, now U.S. Pat. No. 4,439,192, which is in turn a continuation of application Ser. No. 95,975, filed Nov. 20, 1979, now abandoned, which is in turn a continuation of application Ser. No. 869,102, filed Jan. 13, 1978, now abandoned, which is in turn a continuation of application Ser. No. 690,731, filed May 27, 1976, now abandoned.

FIELD OF THE INVENTION

This invention relates to containers for liquids for use in medicine and surgery for example parenteral infusion and medication sets and bags containing blood or blood components.

BACKGROUND OF THE INVENTION

Disposable flexible material bags for these purposes made of two layers of flexible plastics material have been known for a considerable time. The layers derive either from separate sheets or from a flattened sleeve of plastics material. In for example U.S. Pat. No. 2,894,510 there is a typical disclosure of a flattened sleeve heat sealed across spaced-apart positions to define a container between the seals and with a plurality of ducts penetrating the seal at one end by being sealed between the layers. Two of the ducts are additive and outlet ports, respectively, each having a frangible membrane across it so as to isolate the inside of the container from the outside and yet allow efficient access to the contents via a hollow needle inserted through them. A third duct is a comparatively lengthy inlet tube. The ports are not always provided all at one end, see for example U.S. Pat. No. 2,702,034, and this latter also illustrates that there may be any required number of ports. Once the container has been filled via the inlet tube, that tube is sealed off and the whole is sterilized.

The present invention is concerned with the problem of preserving the sterility of the outer ends of the ports, i.e. the ends outwardly beyond the membranes. As far as the inside of the container is concerned there is little problem since the flexibility of the material of the container allows for the expansion which will occur on the heat treatment involved in sterilization, but considerable problems have arisen in conserving the sterility of the outer ends of the ports. In U.S. Pat. No. 2,896,619 for example additional tabs or sheets are secured around the outer end of these ports so as to form a cap over that outer end and this cap is torn open by the user to gain access to the port. However this has involved the provision of extra tabs, i.e. extra parts. These involve an extra manufacturing step and extra material and moreover are not entirely reliable since their securing presents difficulties and the volume which they contain is not entirely reproducible. There have been cases where these protective caps have burst under sterilization or have sprung a leak. Plugs have also been used, see for example U.S. Pat. No. 3,209,752, but are even more likely to be blown off by the expansion of entrapped air.

A similar idea has been applied to preserving the sterility of an inlet port defined by a self-sealing pad on a face of a container; see for example U.S. Pat. No. 2,704,075.

SUMMARY OF THE INVENTION

The present invention is concerned with an efficient and reliable means of allowing for the preservation of the sterility of the outer ends of a port in such a container. In the proposal of the invention, beyond an end of the container volume through which a port penetrates, there is provided an expansion chamber which is defined by a further seal between the layers of material making up the container volume. That is to say when the container is made from a flattened sleeve a first sealed volume is defined by the end seals defining the container and a further sealed volume is defined by securing together the sleeve wall beyond those first mentioned seals at a position where the port opens into it.

Then, the chamber may be opened by being torn off and means such as a line of weakening may be provided to assist this tearing. In a preferred version of the invention all three ducts are provided at one end of the container, the inlet tube being provided between the two ports and symmetrically disposed expansion chambers being provided by extensions of the layers at each side of the tube. The heat-seal defining the ends of the container is preferably of substantial width and may be of greater width at either side of the ports than immediately adjacent those ports so that the line of weakening may pass through heat-sealed areas at each side of each port; then a single tear must tear both layers of the plastics material making up the container.

The expansion volume defined by the chamber may be so great as to obviate the risk of undue expansion during sterilization causing the chambers to burst or to spring a leak and yet the amount of additional material needed is slight and it is integral with the material making up the container.

DESCRIPTION OF DRAWINGS

In order that the invention may be more clearly understood, two embodiments will now be described with reference to the accompanying drawings, wherein.

DESCRIPTION OF PREFERRED EMBODIMENTS

Figure 2:
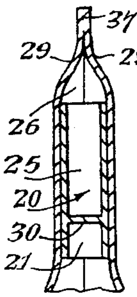
FIGS. 2, 3 and 4 are sections respectively on the lines II—II, III—III, IV—IV in FIG. 1.
Figure 4:
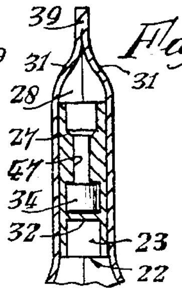
Figure 3:
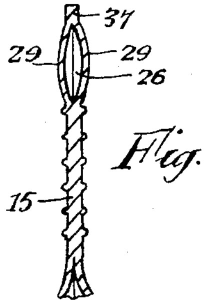
Figure 1:
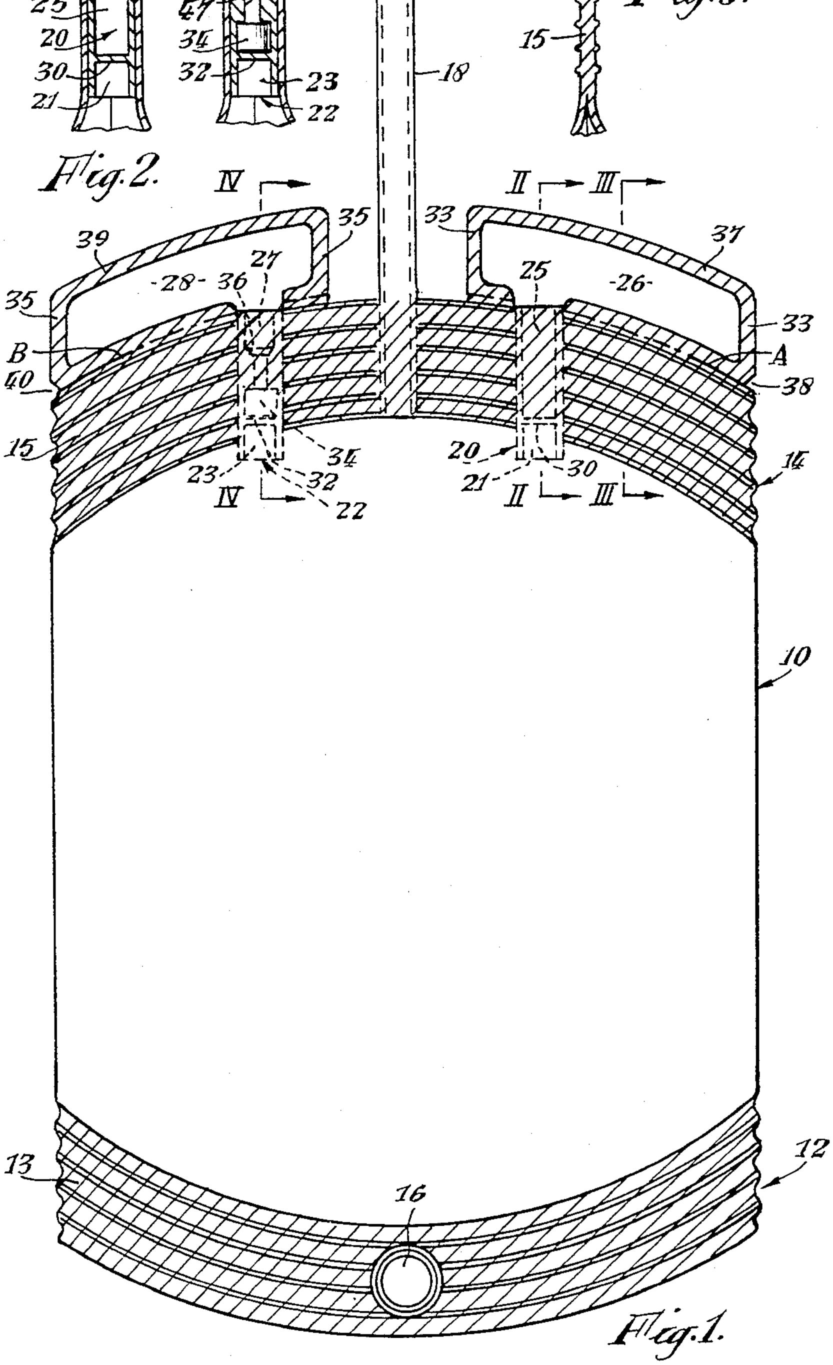
FIG. 1 is a face view of one embodiment of container.

In FIGS. 1 to 4, the container is made from a sleeve of transparent polyvinyl chloride film which has been flattened to form two layers of the film and closed at its longitudinal ends 12,14 by transversely sealing together the layers over the areas shown in hatch lines (in FIG. 1), for example by heat-sealing, preferably by high frequency welding, to form end seals 13,15. At the end 12 an aperture 16 is formed in the seal area. At the other end 14 various ducts enter the interior of the closed container. As shown, these are a filling tube 18, an administration set port 20 and an additive port 22, all of flexible plastics material and all sealed between the layers. The ports communicate at their inner ends 21,23 with the interior of the container. The tube 18 projects outwardly and is an inlet tube used for filling the container with liquid. The outer end of the tube 18 can be sealed, as shown at 24, by welding, the end being cut off before the tube is used for filling the bag, after which the tube is re-sealed by welding. The outer ends 25,27 of the ports 20,22 communicate with respective expansion chambers 26,28. The outer ends 25,27 of the ports are separated from the inner ends 21,23 by frangible membranes 30,32 respectively, formed integrally with the material of the ports (usually polyvinyl chloride with less plasticizer than in the sleeve). The outer ends 25,27 of the ports 20,22 are initially separated by the chambers from the atmosphere and are afforded tamperproof protection. In addition, the port 22 contains as a septum outside the membrane 32 a cylindrical disc 34 of a self-sealing material, e.g. of natural rubber, through which can be inserted a hypodermic needle. A region 47 of uniformly reduced diameter, with a funnel-like lead-in 36, provides a ledge which projects inwardly from the wall of the port 22 just outwardly of the disc 34 to retain it against displacement away from the membrane. The ends of the seal 15 are provided with V-shaped nicks 38,40 to facilitate tearing of the film material along the lines A,B respectively, to expose the outer ends of the ports 20,22.

The walls of the chambers 26,28 are provided by the same layers of film as defined the enclosed container 10 and as were sealed together at the end seals 13,15, the layers having extensions 29,31 (see FIGS. 2, 3 and 4) beyond the end seal 15 and being sealed together at pairs of side seals 33,35 and further end seals 37,39. One member of each pair of side seals is level with the lateral edge of the container, the other adjacent to but free of the tube 18. The width of end seal 15 is greater in its regions remote from the ports 20,22 than in its positions immediately adjacent to them.

After the container has been filled, for example with saline solution, it is sterilised, suitably in an autoclave. During this process any gas in the outer ends of the ports 20,22 expands, and is accommodated in the chambers 26,28. After sterilisation the container can be left sealed, retaining sterility until it is required for use. When appropriate medicament has to be added to the saline solution, the extension 31 of the film material defining chamber 28 is torn away, along the line B starting at the nick 40 to expose the outer end of the port 22. A hypodermic syringe containing the medicament is then used to inject the medicament into the container through the port 22, the needle being guided by the conical lead in 36 and passing through the septum 34 and the membrane 32. The self-sealing material seals around the needle during injection and effectively recloses after removal of the needle preventing contamination and/or loss of the contents of the container. The container is inverted a few times to mix the medicament, and then the extension 29 of the film material is torn away at the other side along the line A, starting at the cut-out 38, to expose the outer end of the port 20. The closure piercing device of the administration set is then inserted into the port 20, the top end of the port being occluded before the leading end of the device pierces the membrane 30. The container is then suspended in an inverted condition from a suitable support by the aperture 16, and it is ready for use.

In a less preferred embodiment the layers will be provided by respective separate sheets of plastics material film, there being side seals as well as end seals.

Figure 5:
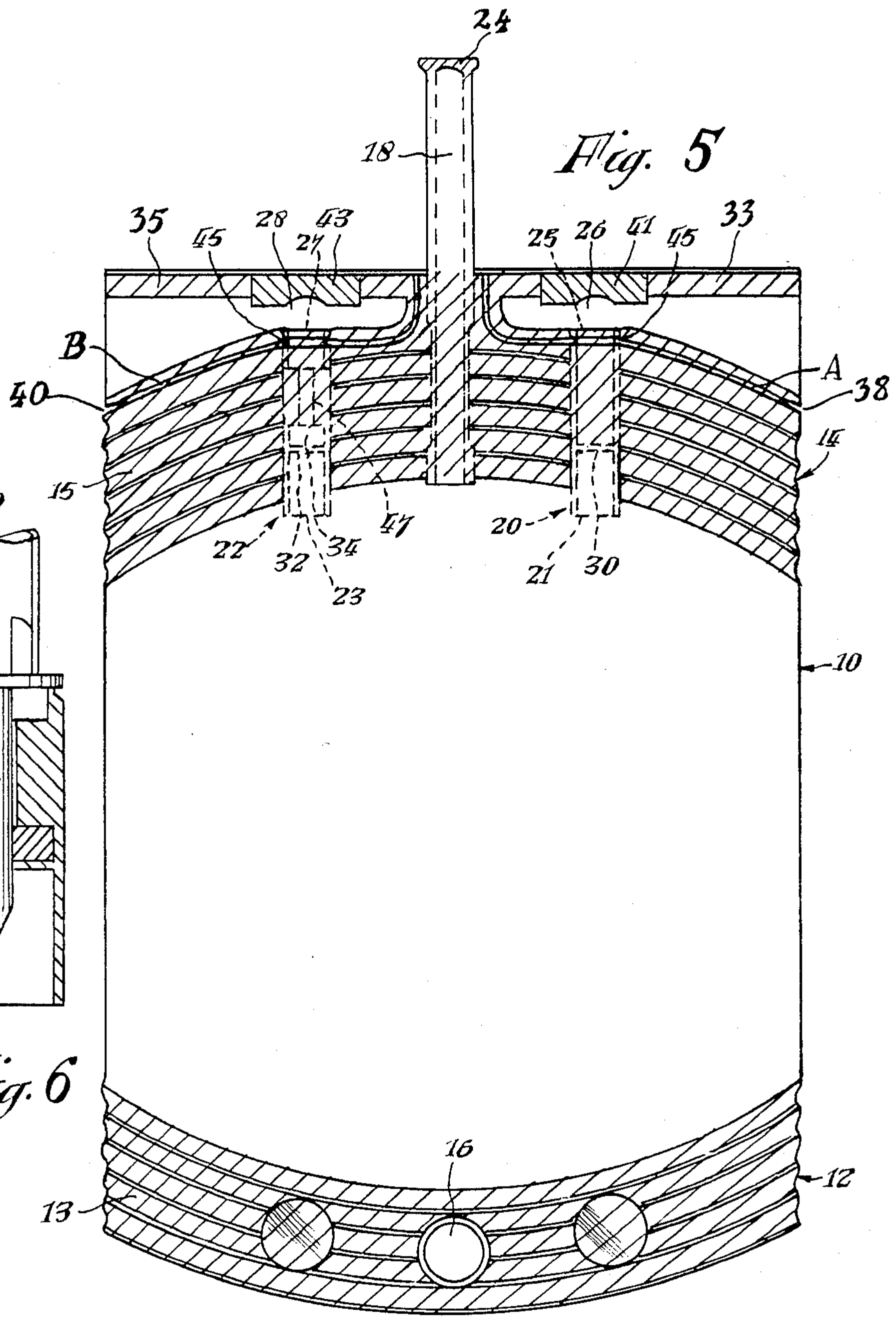
FIG. 5 is a face view of a second embodiment of container.

The embodiment shown in FIG. 5 is in many respects similar to that shown in FIGS. 1 to 4, and like reference numerals are used for similar features. However, the expansion chambers 26,28 are considerably smaller than in FIG. 1. The end seal 15 defines the expansion chambers 26,28 and also leaves unsealed the areas 41,43 at the outer ends of the expansion chambers, these areas being sealed in a separate operation. Lines of weakening A,B are provided by interrupted slits punched through the film material. Where the lines of weakening meet the ports 20,22, the tubular material of the ports is locally thinned at 45 to facilitate rupture thereof. In addition to the aperture 16, two further apertures 16*a* are provided in the corner regions of the end seal 15.

The smaller expansion chambers in this version of the container are generally quite adequate for their purpose.

Figure 6:
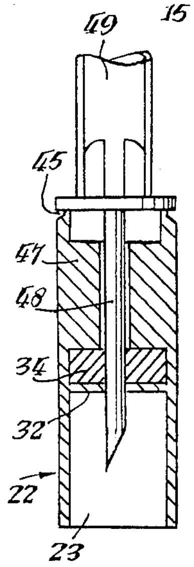
FIG. 6 is an enlarged cross-sectional view of an additive port during addition of medicament to the container.

FIG. 6 shows how an additive medicament can be injected into the container through the additive port 22, by means of a steel needle 48 which passes through the narrow guide region 47 and penetrates the rubber septum 34 and membrane 32. The medicament is supplied to the needle through a supply tube 49.

Various alternative versions of the containers of the present invention can be manufactured, according to the intended use. The embodiments illustrated show a container having an additive port and an administrative port. However, apart from the filling tube, the container may have just one other port, with or without a septum, or it may have two or more ports, any or all of which may be provided with a septum, In some instances, the container may be used for irrigation, rather than for intravenous administration. In such cases, it may be desirable to provide all the ports with a portion of reduced internal diameter so that they cannot be accidentally fitted to an intravenous giving set, which requires the larger internal diameter port 20.

I claim:

1. A container for liquids, comprising:

opposing layers of flexible plastic film, end joints joining said layers of film together at their ends and said layers being enclosed in the longitudinal direction along the sides, between said ends, to define an enclosure for liquid, at least one of said end joints including a peel resistant fusion weld, at least a first portion of which extends continuously across said end joint, at least one duct of plastic material sealed between said layers at said end joint, and extending in the said longitudinal direction, the inner end of said duct communicating with the inside of said enclosure, at least a finite width of said first portion, taken in the axial direction relative to the duct, being non-peelably fusion welded to the exterior of the duct, about its entire circumference, such that the continuous fusion weld is continuous around the circumference of the duct, a rupturable obstruction within the duct, an expansion chamber formed at said end joint, between facing portions of the two layers which are unattached to each other, said expansion chamber communicating with the outer end of the duct, closing means at said end joint which completely and non-peelably encloses said expansion chamber except for its communication with the outer end of the duct, said closing means including, at least in part, said fusion weld, the area of said expansion chamber confined by the layers and the closing means being dimensioned to accommodate during sterilization, without pressure induced film separation at said welds, expansion of gas contained in the combined space of said chamber and the portion of the duct outwardly of said obstruction and communicating with the expansion chamber, means in said first portion of the fusion weld for defining a tear line in said end joint beneath the expansion chamber, exposing the outer end of the duct when the end joint is torn along the tear line, said obstruction being spaced below the tear line, such that at least a part of the said finite width of the first portion, in the region between the tear line and the obstruction, remains after tearing along the tear line.

2. A container according to claim 1, said first portion being continuous with the portion of the fusion weld which forms at least a part of said expansion chamber closing means.

3. A container according to claim 1, said tear line being located, at least in part, above the top of the duct.

4. A container according to claim 1, said opposing layers being opposed sides of a flattened tubular sleeve, wherein a portion of the closing means of said expansion chamber includes the creased side of said sleeve, with the remainder of the closing means of the expansion chamber formed by the fusion weld.

5. A container as claimed in claim 1, wherein said tear line extends laterally in opposite directions from said duct substantially on a line with the end of said outer end of the said duct.

6. A container as claimed in claim 1, comprising two said ducts sealed between the film at said end joint and each associated with its own respective expansion chamber, and a filling tube sealed between the film in said end joint to provide access to the enclosure for filling it with liquid, the two ducts and their associated expansion chambers being located on opposite sides of the filling tube and said expansion chambers being transversely elongate.

7. A container as claimed in claim 6, wherein the obstruction means in one said duct further includes a septum of self-sealing material disposed outside its membrane and adjacent to it, and means being provided in the duct for retaining the septum comprising a parallel sided region of reduced internal diameter outwardly of the membrane to provide also a guide for a needle inserted therein to penetrate the septum and membrane.

8. A container as claimed in claim 1, wherein the duct is of the same material as said film layers and said material is plasticized polyvinyl chloride.

* * * * *